United States Patent [19]

Ito et al.

[11] Patent Number: 5,045,464

[45] Date of Patent: Sep. 3, 1991

[54] ALKALINE CELLULASE AND PROCESS FOR PRODUCING THE SAME

[75] Inventors: Susumu Ito; Shuji Kawai; Shitsuw Shikata; Katsuya Ozaki, all of Utsunomiya; Tadashi Yoshimatsu, Tochigi, all of Japan

[73] Assignee: Kao Corporation, Tokyo, Japan

[21] Appl. No.: 339,592

[22] Filed: Apr. 14, 1989

[30] Foreign Application Priority Data

Apr. 25, 1988 [JP] Japan .................................. 63-101678

[51] Int. Cl.$^5$ ............................................ C12N 9/42
[52] U.S. Cl. ...................................... 435/209; 435/188
[58] Field of Search ................................. 435/188, 209

[56] References Cited

U.S. PATENT DOCUMENTS 4,822,516  4/1989  Suzuki et al. ........................ 435/188

*Primary Examiner*—Herbert J. Lilling
*Attorney, Agent, or Firm*—Oblon, Spivak, McClelland, Maier & Neustadt

[57] ABSTRACT

A novel alkaline cellulase is disclosed. The alkaline cellulase is produced by Bacillus sp KSM-635 (FERM BP-1485) and possesses: (1) $C_x$ enzyme activity to act on carboxymethyl cellulose and weak $C_1$ enzyme $\beta$-glucosidase activities, (2) substrate specificity to act on carboxymethyl cellulose, cellulose cotton, Avicel, filter paper, cellobiose, and p-nitrophenyl cellobioside, (3) a working pH range of 4–12 and an optimum pH range of 9–10, (4) stable pH range of 4.5–10.5 when allowed to stand at 40° C. for 10 minutes, and (5) working temperature range of 10°–65° C. and optimum temperature range at around 40° C. Its activity is not inhibited by chelating agents nor by surface active agents. It is particularly effective as an additive for laundry detergent compositions.

3 Claims, 4 Drawing Sheets

ALKALINE CELLULASE AND PROCESS FOR PRODUCING THE SAME

BACKGROUND OF THE INVENTION

1. Field of the Invention

This invention relates to a novel alkaline cellulase, and, more particularly, to a novel alkaline cellulase having an optimum pH in an alkaline range. The invention also relates to a process for preparing such an alkaline cellulase.

2. Description of the Background

Cellulases are recognized as a group of complex enzymes catalyzing enzymatic reactions decomposing cellulose and analogous polysaccharides into glucose, cellobiose, or into cello-oligosaccharides. Depending on the function, the cellulases encompass enzymes such as $C_1$ enzyme, $C_x$ enzyme, exo-$\beta$-glucanase, endo-$\beta$-glucanase, endo-$\beta$-1,4-glucanase (EC 3.2.1.4) [carboxymethyl cellulase (CMC-ase) or $C_x$ cellulase], exo-$\beta$-1,4-glucanase (EC 3.2.1.91) ($C_1$ cellulase or cellobiohydrolase), $\beta$-1,4-glucosidase (EC 3.2.1.21) (cellobiase or $\beta$-glucosidase), and the like. Conventionally, studies on cellulase have been directed, for the most part, to the effective utilization of biomass resources. For this reason major supply source of cellulase has been fungi belonging to the genera such as Trichoderma, Aspergillus, Acremonium, Humichola, and the like. Cellulases derived from microorganisms, including fungis, however, are different depending on their type with respect to specific actions of component enzymes, as well as in terms of physicochemical characteristics. The exact details have yet to be elucidated.

In recent years, industry has been developing new applications of cellulases, including, for example, the use of cellulases as additives for laundry detergents. Most of the cellulases produced by microorganisms in the natural world, at least those produced by the above-mentioned microorganisms, are acidic cellulases which have an optimum pH range of 4-6. They are deactivated in an alkaline pH range. There are few alkaline cellulases which exhibit maximum activity and resistance in an alkaline pH range, a range which is required for laundry detergents.

The only known processes for producing alkaline cellulases which can be used in laundry detergents are a process for collecting cellulase A from a culture broth of an alkalophilic microorganism belonging to the genus Bacillus (Japanese Patent Laid-open No. 28515/1975), a process for producing alkaline cellulase 301-A through culturing of a microorganism belonging to the genus Cellulomonas (Japanese Patent Laid-open No. 224686/1983), a process for obtaining carboxymethyl cellulase through culturing of an alkalophilic strain, Bacillus No. 1139 [Horikoshi et al, J. Gen. Microbiol., 131, 3339 (1985)], and a process for producing alkaline cellulase using a microorganism belonging to Streptomyces (Japanese Patent Laid-open No. 19483/1986).

Development of an alkaline cellulase which has an optimum pH in an alkaline range and which can be used as an enzyme in laundry detergents has therefore been desired.

In view of this situation, the present inventors have undertaken extensive investigations in order to find alkaline cellulase-producing microorganisms and found that a microorganism belonging to the genus Bacillus, which the inventors discovered and collected from the soil at Hagagun, Tochigi-ken, Japan, could produce a novel alkaline cellulase which is effective as an additive for laundry detergent compositions. This finding has led to the completion of this invention.

SUMMARY OF THE INVENTION

Accordingly, an object of this invention is to provide an alkaline cellulase having the following physicochemical characteristics:

(1) Action

Possesses $C_x$ enzyme activity to act on carboxymethyl cellulose and weak $C_1$ enzyme and $\beta$-glucosidase activities.

(2) Substrate specificity

Acts on carboxymethyl cellulose, cellulose cotton, Avicel, filter paper, cellobiose, and p-nitrophenyl cellobioside.

(3) Working pH range and optimum pH range

Has a working pH range of 4-12 and an optimum pH range of 9-10.

(4) Stable pH range

Stable in a pH range of 4.5-10.5 when allowed to stand at 40° C. for 10 minutes and in a pH range of 6.8-10 when allowed to stand at 40° C. for 30 minutes.

(5) Working temperature range and optimum temperature range

Works in a wide temperature range of 10-65° C., with the optimum temperature range being around 40° C.

(6) Effects of chelating agents.

The activity is not inhibited by EDTA, EGTA, NTA, STPP, and zeolite.

(7) Effects of surface active agents.

The activity is hardly inhibited by surface active agents, including sodium linear-alkylbenzene sulfonate, sodium alkyl sulfate, sodium polyoxyethylenealkyl sulfate, sodium $\alpha$-olefin sulfonate, sodium $\alpha$-sulfonated fatty acid ester, sodium alkyl sulfonate, polyoxyethylene secondary alkyl ether, sodium fatty acid, and dimethyldialkyl ammoniumchloride.

(8) Effects of proteinases

Possesses strong resistance against proteinases.

(9) Molecular weight

Molecular weight determined by gel chromatography is 30,000, 45,000, 90,000, 210,000, 240,000, or 300,000.

In one embodiment the invention provides a process for preparing alkaline cellulase comprising:

culturing a microorganism belonging to the genus Bacillus and capable of producing an alkaline cellulase having varied molecular weight components as endocellulase (CMCase) activity, collecting said alkaline cellulase having varied molecular weight components as endocellulase (CMCase) activity from the culture broth.

Other objects, features and advantages of the invention will hereinafter become more readily apparent from the following description.

BRIEF DESCRIPTION OF THE DRAWING

FIG. 1 is a graph which shows the relationship between the reaction pH and the relative activity of the alkaline cellulase of the present invention, while

DETAILED DESCRIPTION OF THE INVENTION AND PREFERRED EMBODIMENTS

The aforementioned microorganism producing an alkaline cellulase has mycological characteristics discussed below. The following 24 media A-X were employed in experiments for the classification of strains. All of these media contain 1.0% of sterilized sodium carbonate ($Na_2CO_3$).

Composition of Media (% by weight)

Medium A: Bacto peptone, 0.5; meat extract, 0.3; Bacto agar, 1.5

Medium B: Bacto peptone, 0.5; meat extract, 0.3

Medium C: Bacto peptone, 0.5; meat extract, 0.3; NaCl, 7.0

Medium D: Bacto peptone, 0.5; meat extract, 0.3; Bacto gelatin, 20.0

Medium E: Bacto litmus milk, 10.5

Medium F: Bacto peptone, 0.5; meat extract, 0.3; $KNO_3$, 0.1

Medium G: Bacto peptone, 0.7; glucose, 0.5; NaCl, 0.5

Medium H: Bacto peptone, 3.0; meat extract, 0.3; sodium thiosulfate, 0.005; cysteine hydrochloride, 0.02; ammonium iron citrate, 0.05; Bacto agar, 0.5

Medium I: Bacto peptone, 1.5; meat extract, 0.4; lactose, 1.0; sucrose, 1.0; glucose, 1.0; NaCl, 0.5; sodium thiosulfate, 0.008; sodium thiosulfite, 0.04; ferrous sulfate, 0.02; phenol red, 0.002; Bacto agar, 1.5;

Medium J: Bacto peptone, 1.5; yeast extract, 0.5; soluble starch, 2.0; $K_2HPO_4$, 0.1; Bacto agar, 1.5; $MgSO_4.7H_2O$, 0.02

Medium K: ammonium phosphate, 0.1; potassium chloride, 0.02; yeast extract, 0.05; 1.5; $MgSO_4.7H_2O$, 0.02; sugars, 1.0 (sterilized by filtration)

Medium L: dipotassium hydrogenphosphate, 0.1; ammonium dihydrogenphosphate, 0.1; sodium citrate, 0.2; $MgSO_4.7H_2O$, 0.03; NaCl, 0.5; bromothymol blue, 0.0024; Bacto agar, 1.5

Medium M: yeast extract, 0.05; cysteine hydrochloride, 0.01; sodium citrate, 0.3; NaCl, 0.5; sodium thiosulfate, 0.008; ammonium iron citrate, 0.04; glucose, 0.02; potassium dihydrogenphosphate, 0.15; phenol red, 0.0012; Bacto agar, 1.5

Medium N: ammonium phosphate, 0.1; potassium dihydrogenphosphate, 0.05; sodium citrate, 0.2; Bacto agar, 1.5; $MgSO_4.7H_2O$, 0.02

Medium O: yeast extract, 0.05; $Na_2SO_4$, 0.1; $KH_2PO_4$, 0.1; glucose, 1.0; inorganic nitrogen sources, appropriate amount *

\* The medium was adjusted to contain sodium nitrate at a 0.25% concentration, sodium nitrite at a 0.2025% concentration, ammonium chloride at a 0.158% concentration, and ammonium phosphate at a 0.195% concentration (each corresponding to 0.0412 N%).

Medium P: yeast extract, 0.05; $Na_2SO_4$, 0.1; $KH_2PO_4$, 0.1; glucose, 1.0; inorganic nitrogen sources, appropriate amount \*\*; $CaCl_2.2H_2O$, 0.05; $MnSO_4.4-6H_2O$, 0.001; $FeSO_4.7H_2O$, 0.001 (sterilized by filtration); $MgSO_4.7H_2O$, 0.02 (sterilized by filtration)

\*\* The medium was adjusted to contain sodium nitrate at a 0.25% concentration, sodium nitrite at a 0.2025% concentration, ammonium chloride at a 0.158% concentration, and ammonium phosphate at a 0.195% concentration (each corresponding to 0.0412 N%).

Medium Q: King A medium "Eiken" (produced by Eiken Chemical Co., Ltd.), prescribed amount.

Medium R: King B medium "Eiken" (produced by Eiken Chemical Co., Ltd.), prescribed amount.

Medium S: Potato dextrose agar medium (produced by Eiken Chemical Co., Ltd.), prescribed amount.

Medium T: Bacto peptone, 0.25; NaCl, 0.25; yeast extract, 0.25; mannitol, 0.5; Bacto agar, 2.0

Medium U: urea medium "Eiken" (produced by Eiken Chemical Co., Ltd.), prescribed amount.

Medium V: Bacto peptone, 0.1; NaCl, 0.5; $KH_2PO_4$, 0.2; yeast extract, 0.05; glucose, 0.1; urea, 2.0; phenol red, 0.001

Medium W: Bacto peptone, 0.5; yeast extract, 0.5; $K_2HPO_4$, 0.1; glucose, 1.0; $MgSO_4.7H_2O$, 0.02

Medium X: yeast extract, 0.5; glucose, 1.0; casein (Hammerstein, produced by Merck Co.), b 0.5; $K_2HPO_4$, 0.1; $MgSO_4.7H_2O$, 0.02; Bacto agar, 1.5

[Mycological Characteristics]

(1) Microscopic Observation

Cells are gram-positive rods (0.5-1.2 $\mu m \times$ 1.5-4.0 $\mu m$) with an endospore (0.7-1.2 $\mu m \times$ 1.0-2.0 $\mu m$) forming at one of their ends. They have peritrichous flagella and are (2) Growth in various culture media (a) Nutrient agar medium (Medium A)

Colony has a circular shape with the surface being flat. The color of the colony is white-yellow, semi-transparent, and glossy.

(b) Nutrient liquid medium (Medium B)

Cells can grow and the broth Cells exhibit little growth at a neutral pH.

(c) 7% NaCl meat nutrient liquid medium (Medium C) Cells can grow and the broth becomes turbid.

(d) Nutrient gelatin - stab culture (Medium D) Cells do not grow.

(e) Litmus milk culture (Medium E)

Coagulation and peptonization of milk are negative. Litmus color does not change because Medium E is alkaline.

(3) Physiological characteristics (a) Nitrate reduction and denitrification (Medium F)

Nitrate reduction is positive. Denitrification is negative.

(b) MR test (Medium G)

Methyl red color does not change since the medium is alkaline.

(c) VP test (Medium G): positive (d) Indole production (Medium H)

Negative both to an indol-producing test filter paper; Nissan (Trade name, produced by Nissui Seiyaku Co., Ltd.) and to the coloring reaction with Covac reagent.

(e) Production of hydrogen sulfide (Medium I)

Negative (f) Hydrolysis of starch

Hydrolysis of starch was not observed in a normal iodine reaction using a plate agar medium (Medium J), even though the medium was acidified by 4 N hydrochloric acid. Utilization of soluble starch was not observed in the liquid medium (Medium K).

(g) Utilization of citric acid

* Medium K: utilizes citric acid.
* Koser's (Simons) citric acid agar plate medium (Medium L): Cells do not grow. Citric acid utilization was observed in a liquid medium prepared by removing agar from Medium L and adding 0.05% yeast extract.
* Crystensen agar plate medium (Medium M): Cells grow, although no change was observed in phenol red because of alkalinity.
* Medium N: Citric acid is not utilized. Citric acid utilization was observed in a liquid medium prepared by removing agar from Medium N and adding 0.05% yeast extract.

(i) Utilization of inorganic nitrogen

* Medium O: Utilization of nitric acid, nitrous acid, and ammonia is negative or very weak.
* Medium P: Utilization of nitric acid and nitrous acid is strong. Ammonium chloride is utilized only weakly, while ammonium phosphate is utilized normally.

(j) Pigment production

Cells do not grow in King A medium (Medium Q), while in King B medium (Medium R) they turn light yellow, although not fluorescent. Cells grow in potato dextrose agar medium (Medium S) and mannitol yeast extract medium (Medium T) without changing color.

(k) Urease

* Medium U: Cells do not grow. Also, ammonium production was not detected by Nestler reagent in a medium produced by removing phenol red from Medium U.
* Medium V (a medium prepared by adding a yeast extract to Crystensen urea medium): Phenol red was removed from the medium and cells were cultured to confirm ammonia production by Nessler's reagent. The results were negative. Urease activities were negative in Medium V at urea concentrations of 0.1%, 0.2%, 0.5%, 1.0%, and 2.0%.

(l) Oxidase

Unidentified (m) Catalase

Positive (n) Growth conditions (Medium W)

The overall growth temperature range is 20°–45° C., with the optimum growth temperature being 29°–37° C. Experiments using Medium W and $Na_2CO_3$ for changing the initial pH indicated the growth pH range is 8–11 and the optimum pH range is 9.5–10.2. When the pH of the medium was altered using $K_2CO_3$, the growth was feeble, with an optimum pH range being about 9.

(o) Behavior towards oxygen

Aerobic (p) O-F test

Color does not change because of the alkaline conditions. Cells only grow in aerobic conditions.

(q) Sugar utilization (Medium K)

Utilize D-ribose, L-arabinose, D-xylose, D-glucose, D-mannose, D-fructose, maltose, sucrose, trehalose, D-mannitol, inositol, and glycerol, and does not utilize D-galactose, lactose, D-sorbitol, starch, dextrin, or raffinose.

(r) Hydrolysis of casein (Medium X)

Cells were cultured in an agar plate medium (Medium X). Formation of a transparent zone was not observed in the colony periphery by the treatment with 30% trichloroacetic acid, thus showing a negative reaction to casein hydrolysis.

(s) Nutrient Requirement

Requires biotin (or desthiobiotin) for growth.

(t) GC content (Tm method)

The GC content of the strain of this invention was 39.5 mol%.

Based on the above mycological characteristics and after cross-referencing with *Bergey's Manual of Determinative Bacteriology*, (vol 8), the strain was determined to belong to the genus *Bacillus*, a type of ascospore rod. Because of the cell's incapability to grow in a neutral pH and its ability to proliferate in highly alkaline conditions, the strain is considered to be one of the alkalophilic microorganisms recently described by Horikoshi and Akiba [*Alkalophilic Microorganisms*, Japan Scientific Society Press, Tokyo (1982)]. The strain is also distinguishable from known strains of the genus *Bacillus* which grow under neutral conditions.

Since the mycological characteristics of the strain were not identical with any of the already known alkalophilic *Bacillus* microorganisms, this strain was therefore determined to be a novel strain and was named *Bacillus* sp KSM 635. The strain has been deposited with Fermentation Research Institute, Agency of Industrial Science and Technology (FERM BP-1485).

The alkaline cellulase of the present invention can be manufactured by fermentation methods using, for example, *Bacillus* sp KSM-635 (FERM BP-1485), the alkaline aerobe described above.

In the method of the present invention, it is possible to use various other mutants which possess enzyme productivity titers higher than that of the microorganism described above.

To carry out the methods of the present invention, an appropriate medium is sterilized by heating or the like, and *Bacillus* sp. KSM-635 is inoculated into the medium. Shaking culture or aeration/spinner cultivation is carried out for 1-4 days at 22°-40° C., preferably at 26°-37° C. It is preferable to adjust the pH range between 8-11. Frothing occurs in the culture medium, but can be eliminated by the addition of appropriate antifoaming agents.

A culture medium containing an appropriate combination of nitrogen and carbon sources is used. Neither nutrient source is particularly restricted. For example, ammonium nitrate, ammonium sulfate, ammonium chloride, ammonium phosphate, sodium nitrate, corn gluten meal, soy bean flour, corn steep liquor, casamino acid, yeast extract, Pharmamedia, sardine meal, meat extract, peptone, Hypro, Ajipower, corn soybean meal, coffee grounds, cotton seed oil meal, Cultivator, Ajipron, Zest, and the like can be nitrogen sources. For carbon sources, plant fiber substances such as rice husks, wheat bran mash, filter paper, common paper, saw dust, and the like can be used, as well as waste molasses, invert sugar, carboxymethyl cellulose (CMC), Avicel, cellulosic cotton, xylan, pectin, ribose, arabinose, xylose, glucose, mannose, fructose, maltose, sucrose, trehalose, mannitol, inositol, glycerin, acetic acid, citric acid, and the like. In other words, in the method of the present invention, if the medium contains biotin or a derivative of biotin, any medium can be used which possesses a suitable combination of these nitrogen and carbon sources. In addition, inorganic salts such as phosphoric acid, $Mg^{2+}$, $Ca^{2+}$, $Mn^{2+}$, $Zn^{2+}$, $Co^{2+}$, $Na^+$ and $K^+$, and if necessary, inorganic and organic minor nutrient sources can be added.

Separation and purification of the target substance, alkaline cellulase, from the culture broth thus obtained can be performed by any separation and purification methods employed for the separation and purification of common enzymes, as described hereafter in more detail in connection with examples.

For example, the cells and culture liquid is separated from the culture broth by centrifugation, filteration, or the like means. Alkaline cellulase is then separated and collected from the cells and culture liquid by means of conventional procedures, for example, by using protein precipitation methods such as salting out isoelectric point precipitation, or solvent precipitation (in methanol, ethanol, isopropanol, or the like), or by condensation using ultrafilter (for example, Diaflow membrane YC manufactured by Amicon Co.). The ammonium sulfate method (30-70% saturation fraction) is desirable as the salting out method and the ethanol method (concentration of 75%) is desirable as the solvent precipitation method. The alkaline cellulase is collected by filtration, centrifugation, or the like means from the precipitate, and then after desalination dried by freeze-drying, or the like. For the desalination, a commonly used method such as dialysis, gel filtration using Sephadex G-25, or the like is used.

For refining and purifying the alkaline cellulase, appropriate combinations of, for example, hydroxyapatite chromatography, ion-exchange chromatography using DEAE Sepahadex, DEAE Cellulose, or the like, and molecular sieve gel chromatography such as Sephadex or Biogel, can be performed.

Alkaline cellulase of the present invention obtained in this way possesses the physicochemical properties indicated below.

(1) Action

The present enzyme possesses $C_x$ enzyme activity towards carboxymethyl cellulose (CMC). It also demonstrates activity towards phosphoric acid swollen cellulose, cellulose cotton, Avicel, and filter paper. The enzyme hydrolyses cellobiose, cello-oligosaccharide, the artificial substrate p-nitrophenyl cellobioside, and the like, to some degree.

(2) Substrate Specificity

Examples of the substrate specificity of the alkaline cellulase are shown in Table 1. The main activity of the enzyme of the present invention, alkaline cellulase, is towards CMC, however, some hydrolysis activity towards Avicel (SF), filter paper, cellulose cotton, phosphoric acid swollen cellulose, pectin (Citrus), soluble starch (potato), and p-nitrophenyl-$\beta$-D-cellobioside is also present.

TABLE 1

| Substrate | Concentration (%) | Specific activity (unit/mg protein) |
|---|---|---|
| CMC | 1 | 13.5-24.5 |
| Avicel SF | 1 | 0.002-0.045 |
| Filter paper | 2.5 | 0.001-0.052 |
| Cellulosic cotton | 1 | 0.001-0.003 |
| Phosphoric acid swollen cellulose | 1 | 0.60-0.96 |
| Pectin | 1 | 0.004-0.009 |
| Soluble starch | 1 | 0.002-0.005 |
| PNPC* | 0.1 mM | 0.05-0.28 |

*p-nitrophenyl-$\beta$-D-cellobioside

On the other hand, however, it was found that the enzyme had no hydrolytic activity towards alkali (NaOH) swollen cellulose, xylan (larch wood), inulin (dahlia tuber), Curdlan (*Alcaligenes feacalis* var. *myxogenes*), dextrin (corn) and p-nitrophenyl-$\beta$-D-glucoside.

(3) Working pH and optimum pH

The present enzyme functions between the pH range of 4-12, with the optimum range being approximately 9-10.

(4) Stable pH range

Figure 1:
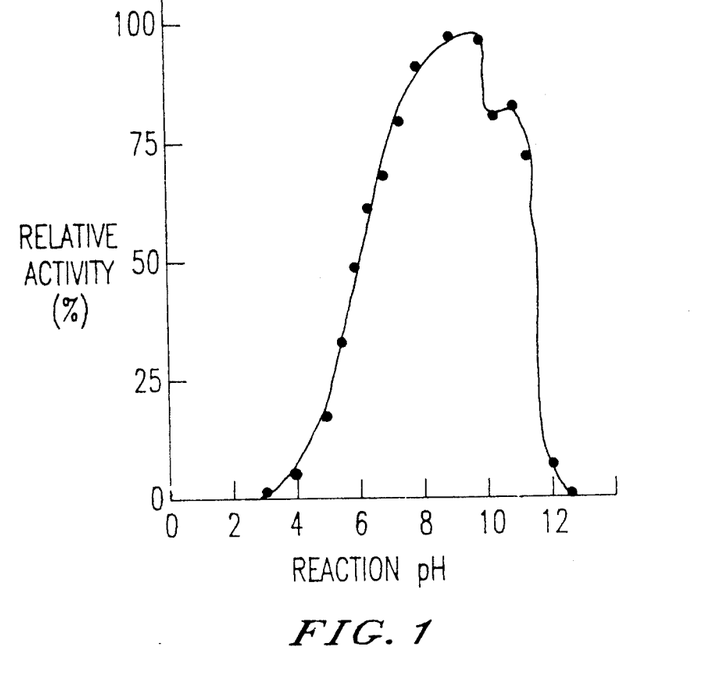
Figure 2:
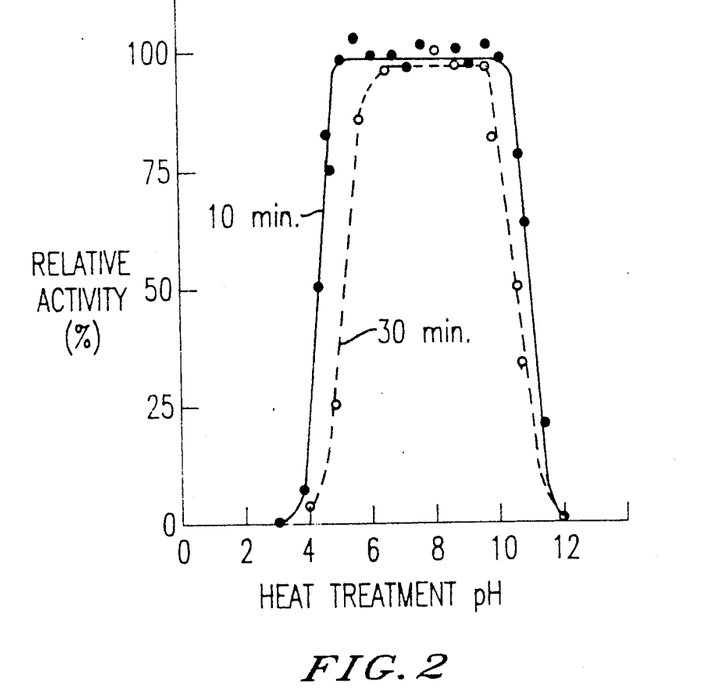
FIG. 2 depicts the relationship between heat treatment pH and residual enzyme activity.

The stable pH ranges in buffer solutions having different pH values at 40° C. when the preparation was left standing for 10 and 30 minutes were found to be 4.5-10.5 and 6.8-10, respectively (FIG. 2). The enzyme preparation showed stability for at least one month when maintained in a buffer solution of a pH range of 4-11 at 5° C.

(5) Working temperature range and optimum temperature range

Figure 3:
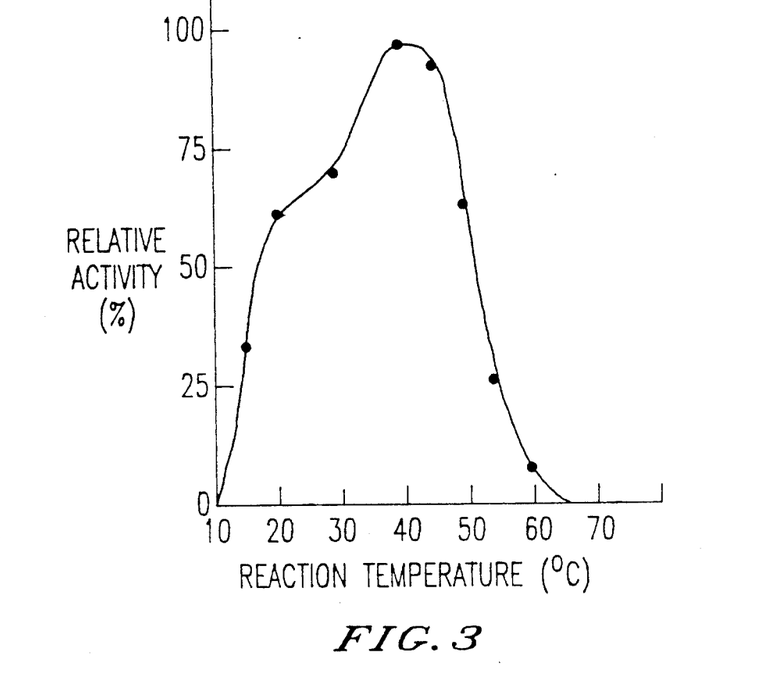
FIG. 3 presents the relationship between the reaction temperature and relative activity, FIG. 4 the relationship between treatment temperature and relative activity, and FIG. 5 the relationship between activity and the Sephacryl S-300 gel chromatography fraction.

The enzyme of the present invention exhibited activity between the temperature range of 10°-65° C. When the reaction was carried out in glycine buffer (pH 9) for 20 minutes, the optimum temperature was about 40° C. (FIG. 3).

(6) Thermal stability

Figure 4:
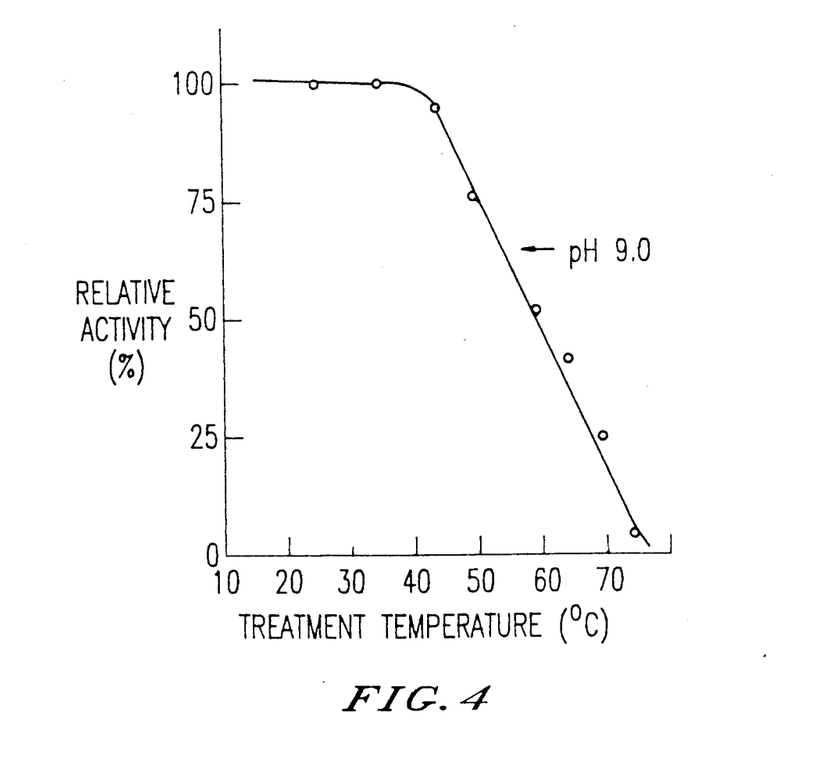

Thermal treatment was carried out at various temperatures in glycine buffer (pH 9) for 20 minutes. It was observed that the present enzyme was not inactivated at all at about 40° C., while at 60° C. and 70° C. approximately 50 and 25%, respectively, residual activity was present (FIG. 4).

(7) Measurement of enzyme activity i) Carboxymethyl cellulase activity 0.1 ml of the enzyme solution was added to a substrate solution composed of 0.2 ml of 2.5% carboxymethyl cellulose (CMC), 0.1 ml of 0.5 M glycine buffer (pH 9.0), and 0.1 ml of deionized water. The reaction was carried out at 40° C. for 20 minutes, following which reducing sugar was determined using the 3,5-dinitrosalicylic acid (DNS) method. In other words, 1 ml of DNS reagent was added to 0.5 ml of the reaction solution, and the mixture was heated and colored for 5 minutes at 100° C. and then cooled. After cooling, 4.5 ml of deionized water was added to dilute the solution and then colorimetry was carried out at a wavelength of 535 nm. Enzyme titer (1 unit) was defined as the amount of enzyme which under the conditions described above generates reducing sugar corresponding to 1 $\mu$mol of glucose in one minute.

ii) p-Nitrophenyl cellobioside degradation activity

After an appropriate amount of the present enzyme was added to 1.0 ml of a reaction solution containing 100 $\mu$mol phosphate buffer (pH 7) and 0.1 $\mu$mol p-nitrophenyl cellobioside (Sigma Co.) at 30° C. and allowed to react, 0.3 ml of 1 M $Na_2CO_3$ and 1.7 ml of deionized water were added. The p-nitrophenol liberated was then measured by colorimetry at a wavelength of 400 nm. The amount of enzyme which liberates 1 $\mu$mol of p-nitrophenol in one minute under these conditions was defined as one unit of p-nitrophenyl cellobioside degradation activity.

iii) Avicelase and FPase activities 0.4 ml of enzyme solution was added to a substrate solution consisting of 0.4 ml of 0.5 M glycine buffer solution (pH 9), 0.4 ml of deionized water, and 20 mg of Avicel (Merck Co. Ltd.) or 20 mg of filter paper (filter paper for determining cellulase activity, Toyo No. 51-Special) fragments (0.5 cm wide by 5 cm long) lumped together by mixing with 0.8 ml of water. The mixture was allowed to react for 20 minutes at 40° C. Avicelase and FPase activities were measured in the same way as for CMCase activity described in i). The amount of enzyme which liberated 1 $\mu$mol of reducing sugar as glucose in 1 minute was defined as one unit of Avicelase and FPase activity. iv) Other activities were measured as described in iii). v) Protein assay was performed with a Bio-Rad Protein Assay Kit (Bio-Rad Co. Ltd.) using bovine serum albumin as a standard protein.

(8) Effects of chelating agents

The most important factor for an enzyme to be used in a detergent is its resistance towards chelating agents in builders, contained within the detergent components. After pretreating alkaline cellulase with EDTA (0.5 mM), EGTA (0.5 mM), NTA (0.5 mM), zeolite (0.05%), and sodium tripolyphosphoric (0.05%), it was found that the residual activity was not inhibited at all.

(9) Effects of proteinases

As a component of detergents, proteinases act to improve the detergency of detergent compositions. Therefore, it goes without saying that if cellulase is added to a detergent containing proteinases, the detergent's strength will increase. In this regard, it is essential that the cellulase be not hydrolyzed by the proteinases and maintain stable activity. Alkaline cellulase possesses strong resistance towards proteinases actually being used in detergents (for example, API-21, Maxatase, Alkalase, and the like) and common proteinases (for example, papain, trypsin, pronase)

TABLE 2

| Proteinase | Residual Activity (%)* |
|---|---|
| nothing added | 100 |
| API-21 (Showa Denko) | 97 |
| Maxatase (Gist-Brocades) | 96 |
| Akalase (Novo) | 96 |
| Papain | 88 |
| Trypsin | 67 |
| Pronase E | 64 |

*Residual enzyme activity was calculated after pretreatment of 50 $\mu$g of alkaline cellulase with 5 $\mu$g of the respective proteinase for 30 minutes at 30° C.

(10) Effects of metals, etc.

Appropriate concentrations of divalent metal ions ($Hg^{2+}$, $Cu^{2+}$, etc.) had inhibitory effects. Slight inhibition was observed for monoiodoacetic acid and para-mercurybenzoate.

(11) Effects of surface active agents

Alkaline cellulase activity was virtually uninhibited by surface active agents (0.5%) such as sodium linear-alkylbenzene sulfonate (LAS) sodium alkyl sulfate ester (ES), sodium polyoxyethylenealkyl sulfate ester (ES), sodium $\alpha$-olefin sulfonate (AOS), sodium $\alpha$-sulfonated fatty acid ester ($\alpha$-SFE), sodium alkyl sulfonate (SAS), polyoxyethylene secondary alkyl ether, sodium fatty acid, dimethyldialkyl ammonium chloride, and the like.

(12) Molecular weight

Figure 6:
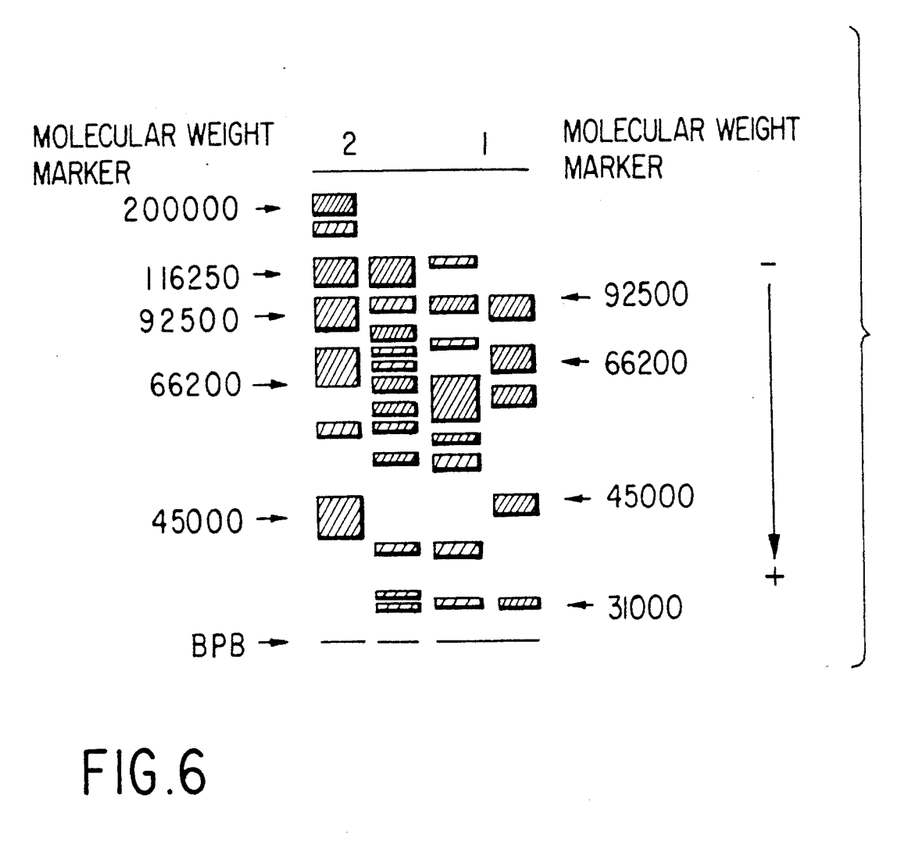
FIG. 6 shows the results of SDS electrophorsis of the alkaline cellulase components CMC I and CMC II.
Figure 7:
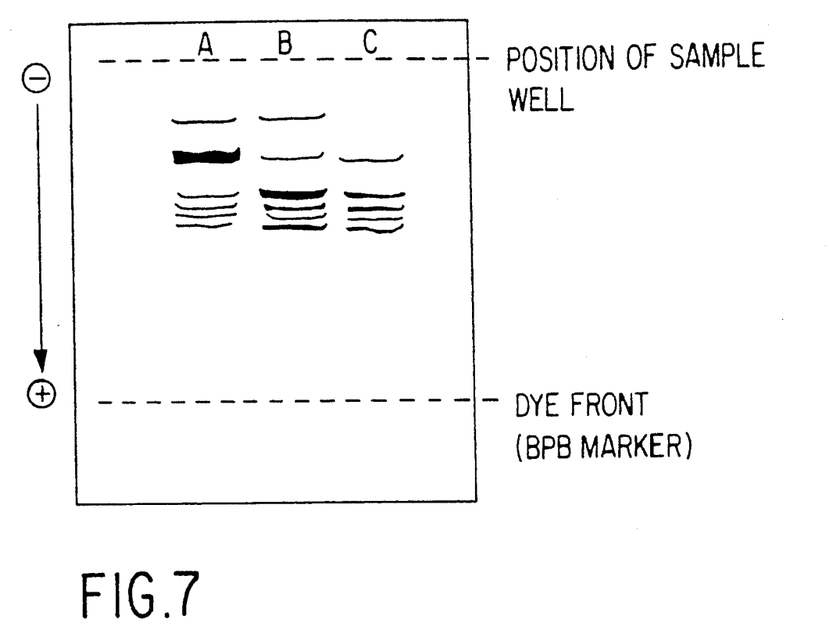
FIG. 7 is the active stain diagram of the alkaline cellulase of the present invention obtained after slab electrophoresis showing the transparent zones obtained from replica plating on an agar plate containing CMC and Congo Red.

The molecular weight of alkaline cellulase of the present invention determined by gel chromatography is approximately 30,000, 45,000, 90,000, 150,000, 180,000, 210,000, 240,000 or 300,000. The microorganism of the present invention produces components of alkaline cellulase having various molecular weights. It is considered that this varied-component molecular weight is due to any or either of (i) degradation of a high molecular weight cellulase, (ii) proteins which are all heterologous, (iii) association between low molecular weight cellulases, or (iv) association between heterologous proteins. The enzyme of the present invention contains single CMCase I (M.W. 145,000 ±10,000) and CMCase II (M.W. 170,000±20,000) (Japanese Patent Application Nos. 257777/1986 and 257778/1986) as determined by polyacrylamide electrophoresis. However, as shown in FIG. 6 when normal SDS electrophoresis was carried out, proteins with a molecular weight ranging from 30,000±2,000 to 120,000±15,000 were stained to produce a ladder pattern. On the other hand, if the alkaline cellulase preparation is replicated on an agar plate containing CMC and Congo Red after it was applied to polyacrylamide electrophoresis, the CMCase active site was detected as at least 5 transparent zones (FIG. 7). FIG. 7 demonstrates the multi-component property of the alkaline cellulase of the present invention.

The characteristics of the alkaline cellulase of the present invention described above are compared to those of other cellulases as follows.

The optimum pH for the present alkaline cellulase is in a high pH range, and it can be distinguished from other cellulases having optimum pH values which range from neutral to acidic values; e.g. those produced by fungi such as *Trichoderma, Penicillium, Aspergillus*

[Kazutoshi Nishizawa, "Cellulase" [published by Tokyo Nankodo, (1974)], *Acremonium* (Japanese Patent Publication No. 166081/1984), *Humicola* (Japanese Patent Publication No. 16316/1986), and the like In addition, when compared to the alkaline cellulase presented in Japanese Patent Publication No. 28515/1975, it can be seen that the physicochemical characteristics of the present alkaline cellulase are clearly different. The present alkaline cellulase possesses at least 5 varied components with molecular weights from 30,000–300,000, while the molecular weights of the cellulases described above are from 15,000–30,000, and the molecular weight of alkaline cellulase produced by the *Bacillus* No. 1139 is 92,000.

At pH 11, the alkaline cellulase of the present invention possesses a relative activity 75–80% of that observed at the optimum pH value. It was found that of all the alkaline cellulases studied in the past, the present enzyme group exhibits the most complete activity in an alkaline pH region. Also, even though the optimum pH is in the high alkaline range, it is important to note that the enzyme possesses activity in the highly acidic pH range of about 4. A cellulase which possesses stability over a wide pH range such as this has not existed in the past. A distinctive feature of this enzyme is that it exhibits full activity even at a low pH. This is the first time that an alkaline cellulase possessing strong resistance towards surface active agents, chelating agents, and proteinases has been presented.

Therefore, the alkaline cellulase of the present invention can be effectively used as an enzyme additive for laundry detergent, as well as for biomass and other uses.

Other features of the invention will become apparent in the course of the following description of the exemplary embodiments which are given for illustration of the invention and are not intended to be limiting thereof.

EXAMPLES

Reference example 1

1 g of soil obtained from Ichikai-machi, Haga-gun, Tochigi-ken, Japan, was suspended in 10 ml of sterilized physiological saline and then heat-treated for 30 minutes at 80° C. This heat-treated solution was diluted appropriately, applied to a master plate [1% meat extract (Oxoid Co.), 1% bacto-peptone (Difco Co.), 1% NaCl, 0.1% $KH_2PO_4$, 0.5% $Na_2CO_3$ and 1.5% bacto agar], and cultured for 3 days at 30° C., resulting in the formation of colonies. Replica plate was carried out by transferring the colonies to sterile agar medium consisting of the same components as the above plate medium except that 2% CMC had also been added. After colonies were formed by culturing at 30° C. for 3–4 days, a Congo Red solution was poured over the plate and colonies. The colonies the periphery of which did not turn a red color were isolated. The colonies selected from the master plate were then screened for high titer CMCase producing bacteria.

*Bacillus sp* KSM-635 (FERM BP-1485) was obtained using the method described above.

Example 1

*Bacillus sp* KSM-635 (FERM BP-1485) was cultured aerobically for 2 days at 34° C. in liquid medium consisting of 1.5% meat extract, 0.5% yeast extract, 1% CMC, 0.1% $KH_2PO_4$, and 0.75% $Na_2CO_3$. To one liter of this culture medium supernatant 3 l of cold ethanol (−10° C.) were gradually added in order to precipitate the proteins. The precipitate thus obtained was dissolved in a small amount of sterilized deionized water, neutralized with dilute acetic acid, and dialyzed with running water for 15 hours. 9.8 g of alkaline cellulase as freeze-dried powder was then obtained.

Example 2

100 ml of medium containing CMC (1%), polypeptone (2%), $KH_2PO_4$ (0.1%), yeast extract (0.1%), and $Na_2CO_3$ (0.75%) was added to a 500 ml conical flask. The medium was sterilized by usual procedures and then inoculated with *Bacillus* sp KSM-635 (FERM BP-1485). The mixture was cultured at 30° C. for 4 days with shaking. After culturing the bacteria were removed by centrifugation and the CMCase activity in the supernatant was determined. The activity was found to be 3,100 units/liter.

Using this supernatant and the same procedure described in Example 1, 9.2 g of alkaline cellulase were obtained.

Example 3

Figure 5:
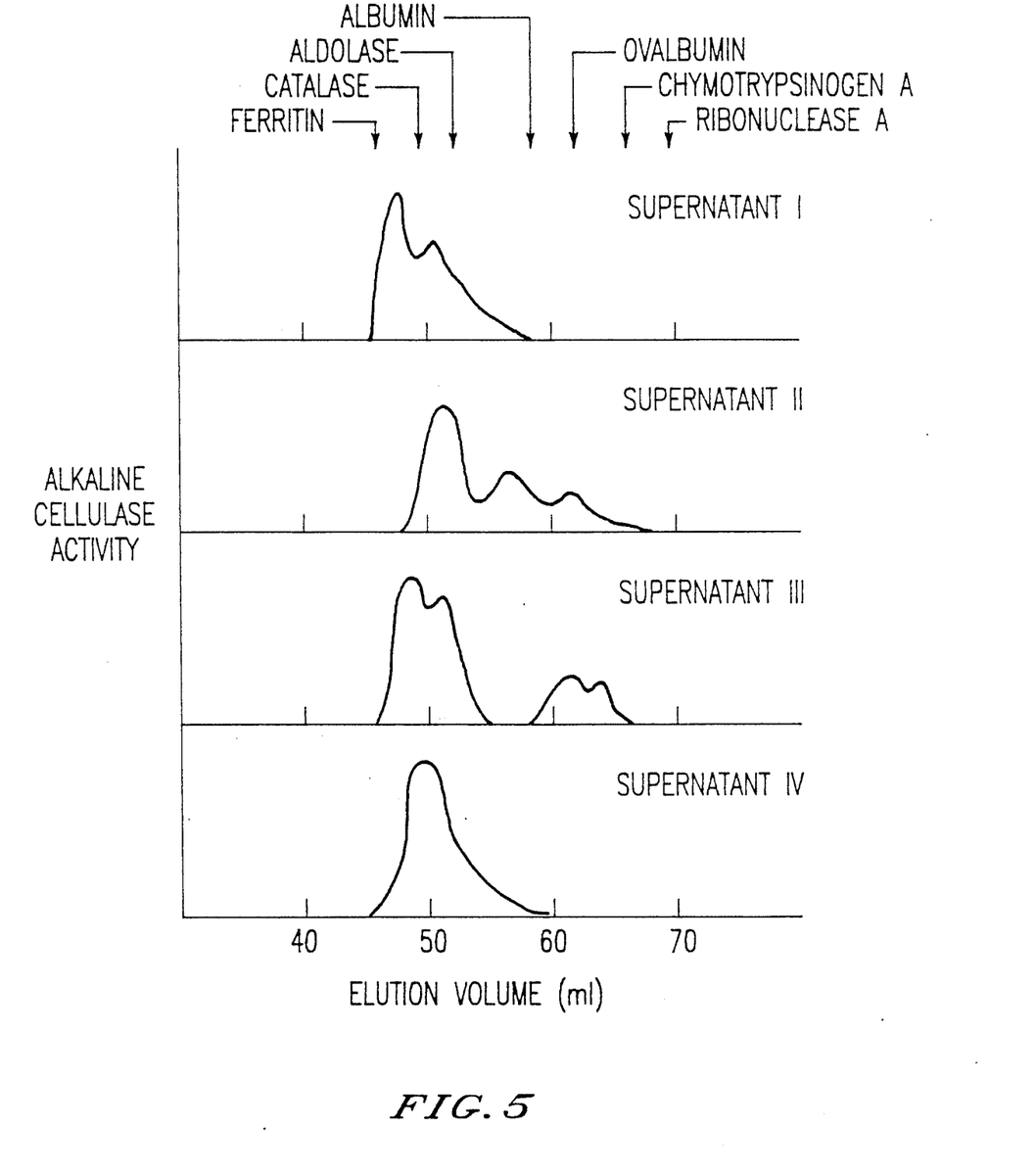

*Bacillus* sp. KSM-635 (FERM BP-1485) was cultured (shaking) for 2 days at 30° C. according to the procedure outlined in Example 2, except that CMC was replaced with 4% sucrose. This operation was repeated a total of 4 times. The culture fluid from each operation was centrifuged, resulting in supernatant samples I, II, III and IV. Using a Sephacryl S-300 column (1.0 × 115 cm) prepared in advance, gel filtration (flow rate: 13 ml/cm².hr) of these samples was carried out and the relationship between the eluted active fraction and molecular weight was examined. Ferritin (M.W. 440,000), catalase (M.W. 232,000), aldolase (M.W. 158,000), albumin (M.W. 67,000), ovalbumin (M.W. 43,000), chymotrypsinogen A (M.W. 25,000) and ribonuclease A (M.W. 13,700) were used as standard proteins and a standard curve showing the relationship between elution volume and molecular weight was prepared. The elution profile obtained for alkaline cellulase is shown in FIG. 5.

Example 4

Supernatants A, B and C were obtained in an identical manner as that described in Example 3. After conducting slab electrophoresis (20 mA constant current) on supernatants A, B and C using 12% polyacrylamide gel (7.3 × 10.3 cm), the gel was replica plated on 0.8% agar plates containing 2% CMC, 100 mM glycine-NaOH buffer (pH 9.0) and 500 mM NaCl. The temperature was maintained at 30° C. for one hour, following which the agar plate from which the gel had been removed was stained for 15 minutes with a 1 mg/ml aqueous Congo Red solution according to the Congo Red method. The cellulase zymogrem was then obtained by rinsing the agar plate for 15 minutes with an aqueous solution of 1 M NaCl (FIG. 7).

Obviously, numerous modifications and variations of the present invention are possible in light of the above teachings. It is therefore to be understood that within the scope of the appended claims, the invention may be practiced otherwise than as specifically described herein.

What is claimed is:

1. An alkaline cellulase having the following physicochemical characteristics:
   (1) Action Possesses $C_x$ enzyme activity to act on carboxymethyl cellulose and weak $C_1$ enzyme and β-glucosidase activities.

(2) Substrate specificity

Acts on carboxymethyl cellulose, cellulose cotton, Avicel, filter paper, cellobiose, and p-nitrophenyl cellobioside.

(3) Working pH range and optimum pH range

Has a working pH range of 4–12 and an optimum pH range of 9–10.

(4) Stable pH range

Stable in a pH range of 4.5–10.5 when allowed to stand at 40° C. for 10 minutes and in a pH range of 6.8–10 when allowed to stand at 40° C. for 30 minutes.

(5) Working temperature range and optimum temperature range

Works in a wide temperature range of 10–65° C., with the optimum temperature range being around 40° C.

(6) Effects of chelating agents.

The activity is not inhibited by EDTA, EGTA, NTA, STPP, and zeolite.

(7) Effects of surface active agents.

The activity is hardly inhibited by surface active agents, including sodium (linear alkyl)benzene sulfonate, sodium alkyl sulfate, sodium polyoxyethylenealkyl sulfate, sodium α-olefin sulfonate, sodium α-sulfonated fatty acid ester, sodium alkyl sulfonate, polyoxyethylene secondary alkyl ether, sodium fatty acid, and dimethyldialkyl ammoniumchloride.

(8) Effects of proteinases

Possesses strong resistance against proteinases.

(9) Molecular weight

Molecular weight determined by molecular sieve gel chromatography is 30,000, 45,000, 90,000, 210,000, 240,000, or 300,000.

2. An alkaline cellulase according to claim 1, which is separated and collected from a culture broth of *Bacillus* sp KSM-635.

3. A process for preparing alkaline cellulase comprising:

culturing a microorganism belonging to the genus *Bacillus* and capable of producing an alkaline cellulase having varied molecular weight components as endocellulase (CMCase) activity, collecting said alkaline cellulase having varied molecular weight components as endocellulase (CMCase) activity from the culture broth.

* * * * *